United States Patent [19]

Bruce

[11] Patent Number: 5,534,000
[45] Date of Patent: Jul. 9, 1996

[54] LASER FIBER APPARATUS HAVING A CONTACT TIP AND ADJACENT DIFFUSER ELEMENT AND SURGICAL METHODS FOR USING SAME

[75] Inventor: Johnny M. Bruce, Magnolia, Tex.

[73] Assignee: Endeavor Surgical Products, Inc., The Woodlands, Tex.

[21] Appl. No.: 210,171

[22] Filed: Mar. 17, 1994

[51] Int. Cl.⁶ ................................................. A61B 17/36
[52] U.S. Cl. ................... 606/15; 606/11; 606/17; 607/89
[58] Field of Search .................. 606/14, 15, 16, 606/17, 10, 11; 607/88, 89

[56] References Cited

U.S. PATENT DOCUMENTS

| | | | |
|---|---|---|---|
| 4,660,925 | 4/1987 | McCaughan, Jr. | 606/15 |
| 5,151,096 | 9/1992 | Khoury | 606/17 |
| 5,169,395 | 12/1992 | Narisco, Jr. | 606/15 |
| 5,196,005 | 5/1993 | Doiron et al. | 606/15 |
| 5,219,346 | 6/1993 | Wagnieres et al. | 606/17 |
| 5,267,995 | 12/1993 | Doiron et al. | 606/15 |

*Primary Examiner*—Stephen C. Pellegrino
*Assistant Examiner*—Sonya Harris-Ogugua
*Attorney, Agent, or Firm*—Workman, Nydegger & Seeley

[57] ABSTRACT

An improved laser fiber assembly is provided which is capable of both effecting direct ablation of tissue or of effecting deep tissue coagulation. The fiber assembly is preferably provided with an orbicular tip for effecting direct ablation in a contact mode. Adjacent the orbicular tip is a cylindrical diffuser element which effects a cylindrical shaped emission pattern when the .orbicular tip is not in contact with tissue. The diffuser element is preferably protected with a covering, such as a teflon tubing element. Alternative embodiments use one or more cylindrical-segment diffuser elements in place of the cylindrical element. The fiber assembly is useful in a wide variety of surgical situations, and is particularly useful for treatment of benign prostatitis hyperplasia. The method of the invention includes the steps of bringing the tip of the dual action fiber assembly into contact with tissue to be ablated or adjacent tissue to be treated for deep tissue coagulation.

19 Claims, 2 Drawing Sheets

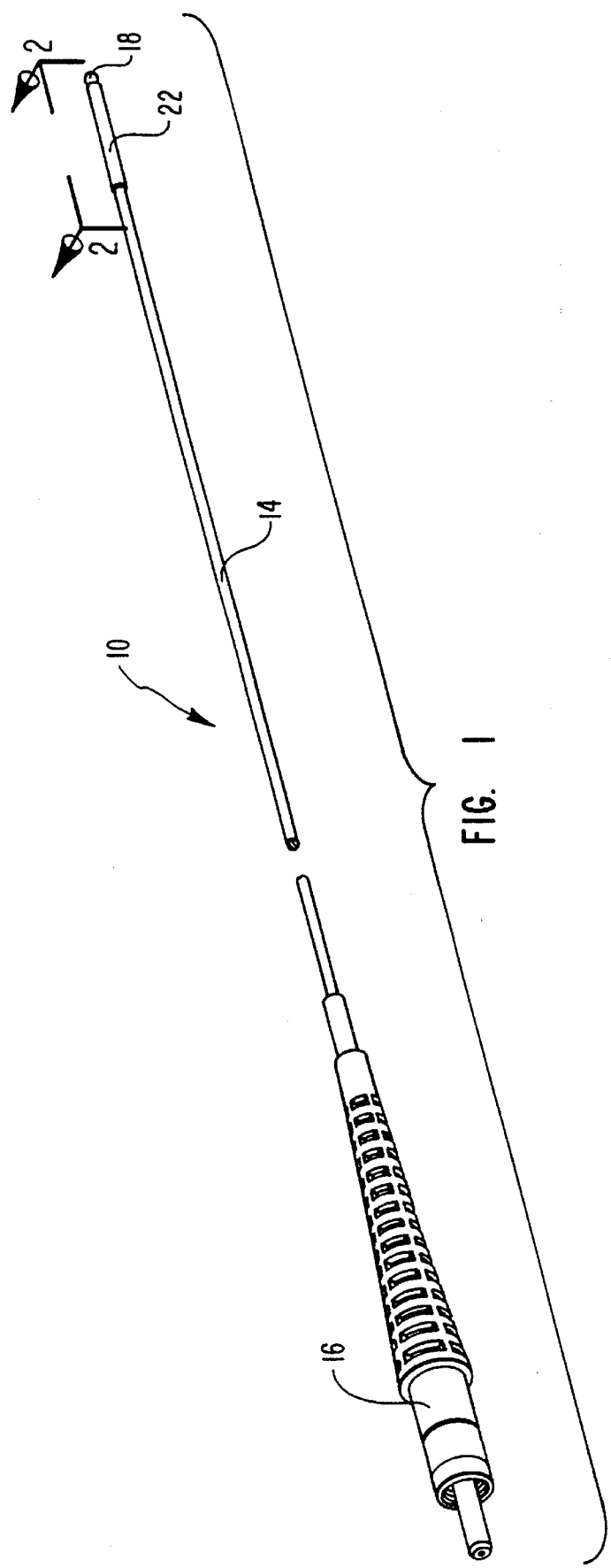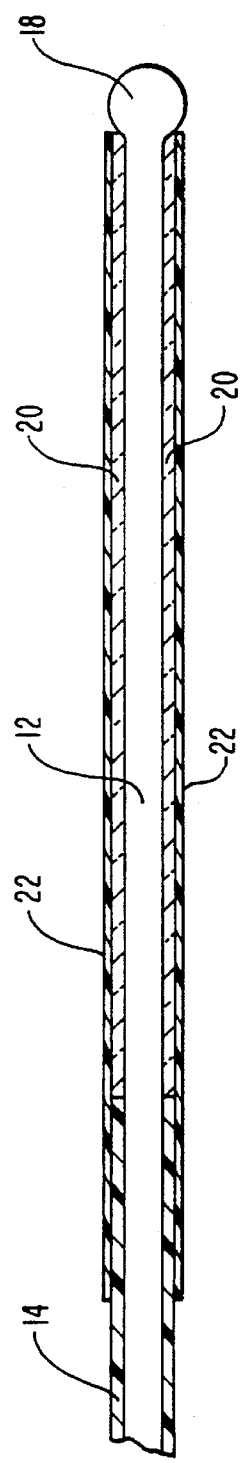

LASER FIBER APPARATUS HAVING A CONTACT TIP AND ADJACENT DIFFUSER ELEMENT AND SURGICAL METHODS FOR USING SAME

BACKGROUND OF THE INVENTION

1. Technical Field

The present invention relates to optical laser fibers and methods of using them in surgical procedures. More particularly, the present invention relates to laser fiber assemblies and methods of using them in the treatment of various surgical procedures involving emission of laser energy in order to effect deep tissue coagulation or direct ablation.

2. Background Information

Optical lasers, such as Nd:YAG lasers, are commonly used in the conduct of surgical procedures. One advantage of laser surgery is that it can often be performed through a relatively small incision or by insertion into an existing body passageway. Laser surgical procedures can frequently be performed on an out-patient basis, resulting in significantly lower cost and less inconvenience to the patient. Dramatic shortening in recovery time is often seen in comparison to traditional surgery which it replaces. For these reasons, substantial effort and expense are being directed toward the development of new laser apparatus and improved methods of surgical treatment using medical lasers.

Various configurations of optical fibers have been developed for different types of surgical procedures. One particularly useful configuration involves contact laser surgery, wherein the tip of an optical fiber assembly is brought into direct contact with tissue desired to be removed, thereby causing it to be cut or vaporized, hereinafter referred to as "ablation". Sometimes, however, ablation is not the most effective means for dealing with a medical problem. Accordingly, an alternative optical fiber assembly often referred to as a "side-firing" fiber has found applications in a variety of situations not readily susceptible to treatment by direct ablation.

A typical side-firing laser optical fiber utilizes a mirror or other optical surface to reflect a laser beam traveling down a fiber so as to emerge from the tip of the fiber at a selected angle. The laser beam is then directed from a short distance onto tissue to be treated. The effect of this treatment is deep tissue coagulation and subsequent tissue necrosis which ultimately results in sloughing off of treated tissue.

One use for which side-firing fibers is currently being tested is in connection with the treatment of benign prostatitis hyperplasia, often referred to as "BPH" for purposes of brevity. BPH is a condition involving an enlarged prostate gland, typically increasing between about two and four times normal size. This condition occurs in approximately one-third of all males over age 60. Currently, approximately 400,000 cases are treated each year in the United States alone, and this number can be expected to increase as the population ages.

BPH is characterized by nocturia (bed-wetting), hesitancy in urination, decreased force of urinary stream, post-voiding dribbling, and a sensation of incomplete emptying. Although incontinence is the most common and emotionally disturbing complaint, it is possible for the enlargement to continue to the point of acute urinary retention. That problem is both painful and dangerous, requiring immediate treatment.

The most common treatment at the present time is known as transurethral resection of the prostate ("TURP"), which involves removal of portions of the prostate gland using a special cytoscope inserted into the urethra. Following a TURP procedure, a typical patient must wait about seven to fourteen days before resuming normal activities, and there is a high incidence of post-operative problems. For example, about 95% of TURP patients experience retrograde ejaculation. It has also been reported that it may take upward of 50 to 100 procedures for an physician to attain true skill at performing TURP procedures; one can only wonder at the fate of the first 50 to 100 patients of each such physician.

Although testing is still far from complete, initial reports indicate that laser treatment of BPH is an improvement over TURP procedures. One such procedure involves the use of side-firing fibers to direct Nd:YAG laser energy onto enlarged prostate tissue. The primary result of this treatment is deep tissue coagulation and subsequent tissue necrosis, which effects a reduction in the size of the prostate over a period of several months following the procedure as the necrotic tissue sloughs off. This technique is reported to be much easier to perform, resulting in proficiency after only five to ten procedures. It also has a much lower reported incidence of problems such as retrograde ejaculation—only about 25% of patients report that adverse side-effect. Hence, it will be appreciated that BPH looms as a major problem for which side-firing laser fibers have shown promise in treating.

Yet, side-firing fibers suffer from drawbacks which require improvement. For example, side-firing fibers are designed to be used in a non-contact mode by generating a relatively broad beam of laser energy that causes deep coagulation and subsequent tissue necrosis rather than a direct ablation of external tissue. Although this is a useful function, it has been discovered that in many procedures, such as BPH, it is often useful to be able to ablate surface tissue for immediate effect rather simply await the delayed effect caused by deep coagulation. Using current technology it is necessary to use a different fiber assembly for direct ablation than is used for deep tissue coagulation.

Another disadvantage of side-firing fibers is the lack of uniform beam intensity at all points at which the beam contacts surrounding tissue. There is also a need to carefully aim the beam at each location wherein it is desired to effect deep tissue coagulation and subsequent tissue necrosis. This requires the fiber to be rotated in order to aim the beam at surrounding tissue. Such rotation requires great care, since it is necessary to irradiate each surrounding portion of tissue for substantially the same period of time in order to insure that the desired effect is obtained. If adequate care is not taken, too much or too little deep tissue coagulation will occur, causing greater or lesser deep tissue necrosis to occur than desired.

SUMMARY OF THE INVENTION

It is a primary object of the present invention to provide improved laser fibers for effecting deep tissue coagulation.

It is another object of the present invention to provide a relatively low-cost fiber assembly that avoids the need to use separate fibers in situations where it is desired to both ablate surface tissue during a surgical procedure effect deep tissue coagulation.

Another object of the present invention is to provide improved fiber assemblies which emit laser energy in a more uniform pattern for effecting deep tissue coagulation.

Yet another object of the present invention is to provide improved fiber assemblies for effecting deep tissue coagulation which need not be rotated during use, thereby easing the task of properly irradiating surrounding tissue in order to obtain uniform deep tissue coagulation.

A further object of the present invention is to provide improved methods for treating BPH and other surgical procedures involving deep tissue coagulation.

Additional objects and advantages of the invention are set forth hereinbelow in the detailed description, or will be appreciated by the practice of the invention.

To achieve the foregoing objects, and in accordance with the invention as embodied and broadly described herein, the present invention provides an improved dual action laser fiber assembly which is capable of effecting both direct ablation of tissue and deep tissue coagulation.

The fiber assembly of the present invention is preferably provided with an orbicular tip for effecting direct ablation when used in a direct contact mode. Located adjacent the orbicular tip is a cylindrical diffuser element which emits laser energy in a cylindrical shaped emission pattern when the fiber is energized with laser energy and the orbicular tip is not in contact with tissue. Alternative embodiments use one or more cylindrical-segment diffuser elements in place of the cylindrical element.

The diffuser element is preferably protected with a covering, such as a teflon tubing element or an optical coating.

The fiber assembly is useful in a wide variety of surgical situations, and is particularly useful for treatment of benign prostatitis hyperplasia. The method of the invention includes the steps of bringing the tip of the dual action fiber assembly into contact with tissue to be ablated or adjacent tissue to be treated for deep tissue coagulation.

BRIEF DESCRIPTION OF THE DRAWING

In the accompanying drawing, which represents the best mode presently contemplated for carrying out the present invention:

FIG. 1 is a partially broken away perspective view of a presently preferred embodiment of a dual action fiber assembly of the present invention.

FIG. 2 is a cross-sectional view of the distal end of the fiber assembly of FIG. 1, taken along the line 2—2.

DETAILED DESCRIPTION OF THE PREFERRED EMBODIMENT

Figure 3:
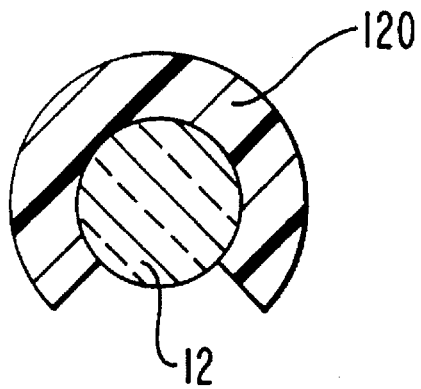
FIG. 3 is a cross-sectional view of an alternative embodiment of a fiber assembly wherein the diffuser element is not cylindrical, but is a large cylindrical-segment.

The present invention is directed to a novel dual action laser fiber assembly and associated methods for conducting laser surgery. The methods and apparatus of the present invention are particularly useful in the practice of benign prostatitis hyperplasia (BPH) and other procedures involving non-contact treatment by a laser beam in order to effect deep tissue coagulation and subsequent necrosis of tissue. However, the novel fiber assembly of the present invention is also able to effect direct ablation of exposed tissue in a contact mode.

FIG. 1 illustrates in perspective view a presently preferred fiber assembly 10 constructed in accordance with the present invention and FIG. 2 shows the emitting tip thereof in cross-section. Preferably, fiber assembly 10 includes an optical fiber 12 (see FIG. 2) which serves as an optical waveguide for delivering laser energy from a medical laser (not shown).

Fiber 12 may be constructed of various materials, but is preferably formed from quartz, silica, or a thermoplastic such as polycarbonate. For typical applications, it is preferred that fiber 12 have a diameter of about 1000 microns, although fibers having other diameters (larger or smaller) may be more useful for particular applications. Fiber 12 should generally be about 3 meters long, although it will be appreciated that other lengths may be used within the scope of the present invention.

Optical fiber 12 is advantageously protected by a reinforcing jacket member 14. Jacket member 14 may be of a conventional construction. A common form of jacket member 14 would include a cladding material surrounding optical fiber 12, and a teflon or nylon coating over the cladding. Jacket member 14 provides mechanical support for fiber 12 so that the fiber will not break during ordinary use, and also protects most of the length of the optical fiber from scratches or other damage which would result in leakage of laser energy. Additionally, the difference in refractive index between fiber 12 and jacket member 14 efficiently directs the laser energy through the fiber waveguide rather than leaking therefrom.

The proximal or input end of fiber assembly 10 is preferably fitted with connector means for optically coupling the input end of the fiber assembly to a medical laser, which serves as a source of laser energy. Preferably, an industry standard SMA-905 connector, designated by reference numeral 16 in FIG. 1, is provided on the input end of the fiber assembly in well-known fashion in order to permit the optical fiber to be readily connected to many brands of medical lasers. Of course, other connectors or means of coupling the fiber assembly to a source of laser energy may also be employed within the scope of the present invention.

The output end of fiber assembly 10 is advantageously provided with tip means for use in effecting direct ablation of tissue with which it is brought in contact. In the most preferred form, fiber assembly 10 is provided with an orbicular tip 18 (see FIG. 2). When using a 1000 micron fiber it is presently preferred that orbicular tip 18 have a diameter of about 2000 microns, although such tip may be larger or smaller in appropriate circumstances. It should also be understood that although an orbicular tip is presently most preferred, the tip means might assume other shapes without departing from the teachings of the present invention, such as tapered or flat or rounded.

It is a further feature of the present invention to provide fiber assembly 10 with diffuser means for emitting laser energy in a diffused pattern. It is presently preferred that the diffuser means comprise a cylindrical diffuser element 20 (see FIG. 2) which is formed around the circumference of optical fiber 12 at a position substantially adjacent to orbicular tip 18. It will be appreciated in view of the discussion contained herein, however, that diffuser element need not be adjacent to the tip of fiber 12, but may be spaced therefrom. It might also prove useful in some circumstances to utilize more than a single diffuser element.

The presently preferred form of diffuser element 20 is constructed by stripping jacket member 14 from the distal end of fiber 12, thereby exposing the optical fiber. It is currently preferred that the length of the stripped area between orbicular tip 18 and the distal end of jacket member 14 be about 2.5 to 3.0 centimeters, although it will be appreciated that other lengths could be utilized without departing from the inventive aspects of the present invention. In practice, the appropriate length of jacket member 14 is most conveniently stripped from optical fiber 12 before forming orbicular tip 18. When jacket member 14 is comprised of conventional cladding and a teflon coating, the coating is stripped from approximately the distal 4 to 6 centimeters, and the underlying cladding is removed by an electric arc device. The exposed section of optical fiber 12 is then cleaned, such as with acetone.

Diffuser element 20 is preferably protected with a suitable optical covering which functions as protective means for protecting the diffuser element from damage. The protective means also functions to insure that pieces of the diffuser element cannot become dislodged from the diffuser element and thereby released into a patient. The presently preferred form of protective means is tube element 22 formed from teflon tubing about 3 centimeters in length. As best seen in FIG. 2, one end of tube element 22 is placed directly against the proximal end of orbicular tip 18 and the other extends past the proximal end of diffuser element 20. The tube element is sized so as to fit tightly over the diffuser element and the distal end of jacket member 14. It is presently preferred that the outside diameter of the tube element be about the same as the diameter of orbicular tip 18 in order to minimize any tendency for the fiber assembly to catch on tissue or on an endoscopic instrument with which the fiber assembly is used.

The presently preferred method of construction of fiber assembly 10 involves taking a 1000 micron optical fiber with the cladding stripped back as discussed above and inserting over it a piece of 14 gauge teflon tubing about 3.5 cm in length. The teflon tubing is then slid back over the jacket member. The optical fiber is cleaved at a position about 3.2 cm from the distal end of jacket member 14, following which an orbicular tip is then formed in conventional fashion, preferably having a diameter of 2000 microns.

The presently preferred diffuser element 20 is prepared by mixing 4 parts of an optical adhesive (Norland Optical Adhesive 61, Norland Products, Inc., New Brunswick, N.J.) with 1 part alumina (Part No. 1344-28-1, 3 micron size particles, Fisher Scientific, Fair Lawn, N.J.). The resultant mixture is advantageously placed into a syringe which is fitted with a blunt tip 23 gauge needle. The teflon tube element 22 is next advanced to the edge of jacket member 14 and the syringe needle tip placed adjacent and facing the tube element. The teflon tube element is then slowly rotated and advanced toward the distal orbicular tip while injecting the adhesive/alumina mixture under the tube element. This process is continued until the tube element is advanced completely so as to rest against orbicular tip 18. After removing any excess adhesive/alumina mixture, the mixture contained under the tube element is cured by exposure to ultraviolet light. This results in preparation of a cylindrical diffuser element about 3 mm in thickness surrounding the entire circumference of optical fiber 12.

The configuration of diffuser element 20 shown in FIG. 2 is advantageous for use in surgical procedures within body passageways, the entire circumference of which will benefit from deep tissue coagulation followed by subsequent necrosis of affected tissue. It has been discovered that in the absence of touching orbicular tip 18 directly to tissue, the difference in the index of refraction between air or irrigation fluid surrounding the orbicular tip results in little or no escape of laser energy from tip 18. Rather, laser energy is uniformly emitted in a cylindrically-shaped pattern along the entire length of diffuser element 20.

Figure 4:
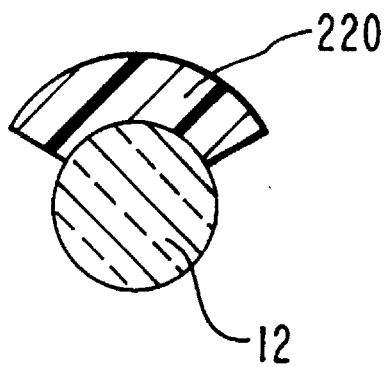
FIG. 4 is a cross-sectional view of yet another embodiment of a fiber assembly wherein the diffuser element is a small cylindrical-segment.

It is not always desirable that diffuser element 20 surround the entire circumference of optical fiber 12. For example, it may at times occur that a surgical procedure will be performed wherein only a portion of surrounding tissue is desired to be treated by diffused emission for deep tissue coagulation. In such circumstances it would be more preferable to utilize a diffuser element having shapes other than cylindrical. For example, FIG. 3 shows in cross-section a fiber assembly utilizing a diffuser element 120 which is formed about most, but not all of the associated optical fiber 12. FIG. 4 shows in cross-section another embodiment in which diffuser element 220 is formed about only a relatively small portion of the circumference of optical fiber 12. The partially cylindrical constructions like that of FIGS. 3 and 4 shall sometimes hereinafter be referred to by the term "cylindrical-segment".

Cylindrical-segment configurations such as shown in FIGS. 3 and 4 will generate a fan-shaped emission pattern corresponding in shape to the diffusion element. A cylindrical-segment diffuser element will have substantially uniform power density throughout its emission pattern.

Figure 5:
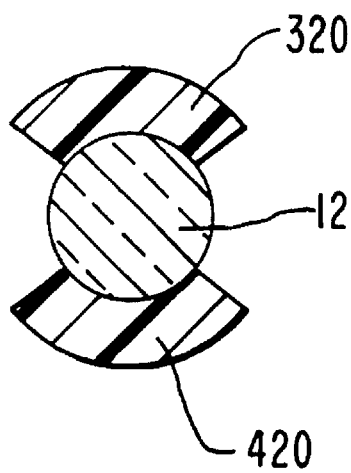
FIG. 5 is a cross-sectional view of another embodiment of a fiber assembly in which two small cylindrical-segment diffuser elements are used.

FIG. 5 illustrates in cross-section yet another embodiment of a fiber assembly in which two diffuser elements 320 and 420 are used in place of a single diffuser element. The two cylindrical-segment diffuser elements of FIG. 5 are situated on opposite sides of fiber 12, but it should be understood that alternative arrangements could be used. The configuration of FIG. 5 will emit laser energy on both sides of fiber 12, but not in between.

From the teachings of FIGS. 3–5, it will be appreciated that appropriate selection of one or more cylindrical-segments having selected cylindrical-segment shapes and lengths will provide a wide variety of uniform emission patterns not available using conventional technology.

Figure 6:
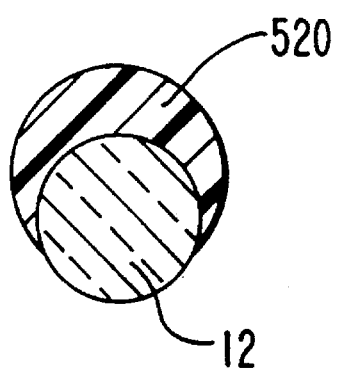
FIG. 6 is a cross-sectional view of another embodiment of a fiber assembly using a diffuser element segment which is tapered at the edges thereof.

The embodiments of FIGS. 3, 4 and 5 are not illustrated as being provided with protective means for protecting the diffuser element. Nevertheless, it is to be understood that protective means may be provided, and is in fact preferred. It may be desired to utilize a tube element corresponding to tube element 22, even though such a tube element will not conform perfectly to the exposed fiber at the locations immediately adjacent to the diffuser element cylindrical-segment. Alternatively, other protective means could be utilized, such as application of an optically clear coating. Yet another alternative could involve formation of the edges of the diffuser element so as to be tapered or rounded (See, e.g., diffuser element 520 of FIG. 6) in a fashion which permits a teflon tube element to readily conform to both the diffuser element and the optical fiber.

An optical fiber assembly constructed in accordance with the foregoing is more useful than a side-firing fiber for use in effecting deep tissue coagulation and necrosis. Unlike conventional side-firing fibers wherein it is necessary to carefully aim a laser beam for appropriate time intervals at adjacent locations on a patient's tissue in order to avoid overexposing some tissue and underexposing other tissue, the present invention is well suited to simply placing the diffuser element at a desired location and activating the laser for a suitable interval. All surrounding tissue will be evenly irradiated without requiring undue care or attention to aiming and moving. This greatly improves safety and efficacy as well as ease of use.

Notwithstanding the substantial benefits of the diffuser element technology discussed above to effect deep tissue coagulation, it is a further advantage of the present invention that when orbicular tip 113 is brought into contact with tissue, laser energy will emit directly from the contacting surface, thereby efficiently ablating tissue with which it is brought into contact. This feature allows a fiber assembly prepared in accordance with the present invention to serve as a dual action fiber assembly. That is, a single fiber assembly can effectively function as both a contact fiber for direct ablation of tissue, or as a non-contact fiber for use in effecting deep tissue coagulation. This combination permits a great deal of flexibility not previously available.

It will be readily appreciated that the fiber assembly of the present invention will be useful in numerous surgical procedures. A presently preferred use of the fiber assembly of the present invention is in the treatment of BPH. In order to treat BPH, a suitable optical fiber assembly 10 is selected for use with an endoscopic instrument. The term "endoscopic instrument" is to be understood broadly, encompassing not only endoscopes, but also cytoscopes and other instruments used for introducing a laser fiber into a surgical site under visual control. The endoscopic instrument is fitted with optical fiber assembly 10 and then inserted through the patient's urethra and advanced to the location of the enlarged prostate. To accommodate use with an endoscope or cytoscope small enough to be inserted into a urethra, optical fiber 12 should preferably be 1000 microns in diameter, or less. Taking care to prevent the orbicular tip of the fiber from touching the surrounding tissue, the laser is activated so that a diffused laser beam is emitted onto a surrounding area of tissue requiring deep tissue coagulation. If the surgeon observes a blockage or tissue that would better be removed directly rather than in a deep tissue coagulation fashion, the orbicular tip may be brought directly into contact with the tissue to be removed, and the laser operated in order to effect immediate ablation of the tissue.

From the foregoing, it will be appreciated that the present invention provides substantially improved laser fiber assemblies affording greater options and flexibility to a surgeon while also providing improved safety and efficacy. The present invention provides a relatively low-cost fiber assembly that avoids the need to use a separate fiber in situations where it is desired to ablate surface tissues during a surgical procedure using a side-firing fiber. It also provides fiber assemblies which need not be rotated during use, thereby easing the task of evenly irradiating surrounding tissue with laser energy in order to obtain uniform deep tissue coagulation. It further provides substantially improved methods for treating BPH and other surgical procedures.

It is to be understood that the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by United States Patent is:

1. A laser fiber assembly for use in performing laser surgical procedures, comprising:

an optical fiber, said optical fiber having an input end and an output end;

connector means for coupling the input end of said optical fiber to a laser source;

tip means at the output end of said optical fiber for direct ablation of tissue with which said tip means may be brought in contact while emitting laser energy;

diffuser means secured to the optical fiber for emitting substantially all input laser substantially all input energy in a diffused pattern when laser energy is directed into the input end of the optical fiber and while the tip means is not in contact with tissue.

2. A laser fiber assembly as defined in claim 1, wherein the diffuser means is situated adjacent to the tip means.

3. A laser fiber assembly as defined in claim 1, wherein the diffuser means is cylindrical.

4. A laser fiber assembly as defined in claim 1, wherein the diffuser means is a cylindrical-segment.

5. A laser fiber assembly as defined in claim 1, wherein the diffuser means comprises a plurality of cylindrical segments.

6. A laser fiber assembly as defined in claim 1, wherein the diffuser means comprises a diffuser element formed of a mixture of optically clear adhesive and alumina secured to the optical fiber.

7. A laser fiber assembly as defined in claim 1, wherein the tip means is an orbicular tip.

8. A laser fiber assembly as defined in claim 1, further comprising protective means for protecting the diffuser means.

9. A laser fiber assembly as defined in claim 8, wherein the protective means is a tube member secured over the diffuser means.

10. A laser fiber assembly for use in performing laser surgical procedures, comprising:

an optical fiber, said optical fiber having an input end and an output end;

connector means for coupling the input end of said optical fiber to a laser source;

tip means at the output end of said optical fiber for direct ablation of tissue with which said tip means may be brought in contact while emitting laser energy;

a cylindrical diffuser element affixed to the optical fiber in order to emit laser energy in a diffused pattern when said fiber is energized with laser energy and when the tip means is not in contact with tissue.

11. A laser fiber assembly as defined in claim 10, wherein the diffuser means is situated adjacent to the tip means.

12. A laser fiber assembly as defined in claim 10, wherein the diffuser means comprises a diffuser element formed of a mixture of optically clear adhesive and alumina secured to the optical fiber.

13. A laser fiber assembly as defined in claim 10, wherein the tip means is an orbicular tip.

14. A laser fiber assembly as defined in claim 10, further comprising protective means for protecting the diffuser means.

15. A laser fiber assembly as defined in claim 10, wherein the protective means is a tube member secured over the diffuser means.

16. A method for effecting laser surgery comprising the steps of:

obtaining a dual action laser fiber assembly as defined in claim 1 and a suitable laser source;

successively situating the diffuser means adjacent to tissue in which it is desired to effect deep tissue coagulation and tissue necrosis and bringing the tip means into contact with tissue to be ablated; and energizing the laser source so as to emit laser energy through the tip means when in contact with tissue and from the diffuser means when the tip means is not in contact with tissue.

17. A method as defined in claim 16, further comprising the steps of:

obtaining an endoscopic instrument suitable for insertion into the urethra of a patient suffering from benign prostatitis hyperplasia;

inserting said endoscopic instrument into the urethra of a patient suffering from benign prostatitis hyperplasia in order to place the diffuser means adjacent a region of the patient's prostate where it is desired to effect deep tissue coagulation; and activating the laser source.

18. A method for effecting laser surgery comprising the steps of:

obtaining a dual action laser fiber assembly having a contact tip for effecting direct ablation of tissue and a diffuser element for effecting deep tissue coagulation and a suitable laser source;

successively situating the diffuser element adjacent tissue in which it is desired to effect deep tissue coagulation and tissue necrosis and bringing the contact tip into contact with tissue to be ablated; and energizing the laser source so as to emit laser energy through the contact tip when in contact with tissue and from the diffuser element when the contact tip is not in contact with tissue.

19. A method as defined in claim 18, further comprising the steps of:

obtaining an endoscopic instrument suitable for insertion into the urethra of a patient suffering from benign prostatitis hyperplasia;

inserting said endoscopic instrument into the urethra of a patient suffering from benign prostatitis hyperplasia in order to place the diffuser element adjacent a region of the patient's prostate where it is desired to effect deep tissue coagulation; and activating the laser source.

\* \* \* \* \*

UNITED STATES PATENT AND TRADEMARK OFFICE
CERTIFICATE OF CORRECTION

PATENT NO. : 5,534,000
DATED : July 9, 1996
INVENTOR(S) : Johnny M. Bruce

It is certified that error appears in the above-indentified patent and that said Letters Patent is hereby corrected as shown below:

Title page, item [57], line 7, "orbicular" should be --orbicular--.
Column 2, line 7, "an physician" should be --a physician--.
Column 2, line 34, "rather simply" should be --rather than simply--.
Column 2, line 60, "procedure effect" should be --procedure and effect--.
Column 7, line 4, "tip 113" should be --tip 18--.

Signed and Sealed this

First Day of July, 1997

Attest:

BRUCE LEHMAN

Attesting Officer

Commissioner of Patents and Trademarks